United States Patent
Glenn, Jr. et al.

(10) Patent No.: US 6,936,264 B2
(45) Date of Patent: Aug. 30, 2005

(54) DELIVERY OF REACTIVE AGENTS VIA MULTIPLE EMULSIONS FOR USE IN SHELF STABLE PRODUCTS

(75) Inventors: Robert Wayne Glenn, Jr., Virginia Water (GB); Anthony McMeekin, Chertsey (GB); George Endel Deckner, Cincinnati, OH (US); Tharwat Tadros, Wokingham (GB)

(73) Assignee: The Procter & Gamble Company, Cincinnati, OH (US)

( * ) Notice: Subject to any disclaimer, the term of this patent is extended or adjusted under 35 U.S.C. 154(b) by 260 days.

(21) Appl. No.: 09/799,185

(22) Filed: Mar. 5, 2001

(65) Prior Publication Data

US 2002/0155080 A1 Oct. 24, 2002

(51) Int. Cl.$^7$ .............................. A61K 6/00; A61K 9/00; A61K 7/06; A61K 7/09; A61K 31/74
(52) U.S. Cl. .................. 424/401; 424/400; 424/70.1; 424/70.2; 424/70.6; 424/78.02; 424/78.03; 514/880; 514/937
(58) Field of Search ................. 424/400, 401, 424/70.1, 70.2, 70.6, 78.02, 59, 61, 62, 63, 78.03, 70.5; 514/844, 880, 937, 947, 938

(56) References Cited

U.S. PATENT DOCUMENTS

| | | | | |
|---|---|---|---|---|
| 5,087,733 A | * | 2/1992 | Deppert et al. | 560/147 |
| 5,229,105 A | * | 7/1993 | Wilmsmann | 424/59 |
| 5,525,332 A | * | 6/1996 | Gough et al. | 424/70.12 |
| 5,651,793 A | * | 7/1997 | Hoeffkes et al. | 8/406 |
| 5,948,855 A | | 9/1999 | Lin et al. | |
| 6,171,600 B1 | * | 1/2001 | Dahms | 424/401 |
| 6,238,657 B1 | * | 5/2001 | Lin et al. | 424/70.12 |

FOREIGN PATENT DOCUMENTS

| | | |
|---|---|---|
| EP | 0 717 978 A2 | 6/1996 |
| EP | 0 782 846 A2 | 7/1997 |
| EP | 1069150 A2 | 1/2001 |
| JP | 11128713 * | 5/1999 |
| WO | WO-97/17938 A1 | 5/1997 |
| WO | WO-00/40209 A2 | 7/2000 |

* cited by examiner

Primary Examiner—Sharmila S. Gollamudi
(74) Attorney, Agent, or Firm—Brahm J. Corstanje; Michael J. Sambrook; Brian M. Bolam

(57) ABSTRACT

Emulsion treatment compositions comprise an aqueous continuous phase and a discontinuous phase in the form of an oil-in-oil emulsion. The oil-in-oil emulsion comprises a reactive component including a reactive agent and an internal oil, wherein the internal oil solubilizes the reactive agent, and a middle oil in which the reactive component is dispersed. The middle oil is immiscible with the internal oil, does not solubilize the reactive agent, is immiscible in the aqueous continuous phase, and includes a hydrophobic particulate thickener. Methods for treating hair comprise applying the emulsion treatment compositions to hair.

22 Claims, No Drawings

DELIVERY OF REACTIVE AGENTS VIA MULTIPLE EMULSIONS FOR USE IN SHELF STABLE PRODUCTS

FIELD OF INVENTION

The present invention relates to a system for the delivery of reactive cosmetic actives (such as reactive conditioners, dyes, styling aids, sunscreens etc.) to amino acid based substrates from a chemically shelf stable formulation.

BACKGROUND OF THE INVENTION

Consumers have been treating amino acid based substrates for years. Such treatments have included the waterproofing or coloring of textiles, the sunscreening of skin, the coloring, conditioning, and styling of hair, the dentifrice treatment of teeth, and more. It is well known that if such treatments can be done by a safe covalent attachment to the substrate, that the treatment will be much more long lasting. Therefore, several reactive chemistries have been developed to provide covalent attachment to amino acid based substrates such as hair. Historically, these technologies, based on covalent attachment of cosmetic actives, have primarily relied upon electrophilic (electron accepting) and nucleophilic (electron donating) reactive groups or "hooks". More recently, a Protected Thiols "hook" technology for the covalent attachment of cosmetic actives to amino acid substrates has been proposed.

It is highly desirable to formulate consumer products as aqueous solutions or aqueous emulsions for a number of consumer preferred attributes, e.g., ease of rinsing, aesthetic feel, less coating of bathroom tiles, environmental concerns, etc. However, attaining such aqueous compositions is problematic in the delivery of technologies for the covalent attachment of cosmetic actives to amino acid based substrates. The reactive groups or "hook" moieties which are reactive towards amino acid residues in hair protein are also reactive towards electron rich ingredients that are employed in the formulation of consumer products to deliver these actives, including water and even atmospheric oxygen. This leads to pre-mature decomposition of the hooks of covalent reactive compounds, referred to herein as reactive agents, over the shelf life of the product which severely or completely mitigates reactive efficacy with a substrate upon usage by the consumer.

While the prior art delivery systems have addressed some of the problems of achieving covalent attachment of cosmetic actives to amino acid based substrates, they have not addressed the problems to the extent of or in the manner of the present invention, and there is a continuing need for additional improved delivery system approaches that will enable the formulation and delivery of reactive agents to amino acid based substrates from an aqueous composition that is chemically shelf stable.

SUMMARY OF THE INVENTION

The present invention is directed to emulsion treatment compositions which comprise (a) an aqueous continuous phase; and (b) a discontinuous phase in the form of an oil-in-oil emulsion which comprises (i) a reactive component including a reactive agent and an internal oil, wherein the internal oil solubilizes the reactive agent, and (ii) a middle oil in which the reactive component is dispersed, wherein the middle oil is immiscible with the internal oil, does not solubilize the reactive agent, is immiscible in the aqueous continuous phase, and includes a hydrophobic particulate thickener.

The present invention is further directed to emulsion treatment compositions which comprise (a) from about 50% to about 85%, by weight of the emulsion treatment composition, of an aqueous continuous phase; and (b) from about 10% to about 50%, by weight of the emulsion treatment composition, of a discontinuous phase in the form of an oil-in-oil emulsion which comprises (i) a reactive component including from about 1% to about 5%, by weight of the emulsion treatment composition, of a reactive agent and from about 25% to about 60%, by weight of the oil-in-oil emulsion, of an internal oil, wherein the internal oil solubilizes the reactive agent, and (ii) from about 40% to about 60%, by weight of the oil-in-oil emulsion, of a middle oil in which the reactive component is dispersed, wherein the middle oil is immiscible with the internal oil, does not solubilize the reactive agent, is immiscible in the aqueous continuous phase, and comprises from about 5% to about 15%, by weight of the middle oil, of a hydrophobic particulate thickener.

The present invention is further directed to methods for treating hair by applying an effective amount of such compositions to hair.

These and other features, aspects, and advantages of the present invention will become evident to those skilled in the art from a reading of the present disclosure.

DETAILED DESCRIPTION

While the specification concludes with claims, which particularly point out and distinctly claim the invention, it is believed the present invention will be better understood from the following description.

The present invention relates to the delivery of reactive agents via multiple emulsions for use in chemically shelf stable products.

The term "amino acid based substrates", as used herein, refers to proteinaceous materials, such as keratin, as found in human and animal hair, skin, and nails. Amino acid based substrates useful herein are hydroxyl-containing, amine-containing, thiol-containing, and disulfide-containing amino acids.

The term "covalently reactive", as used herein, refers to the ability of reactive agents to form covalent bonds with functional groups within proteinaceous keratin, e.g., with keratin amino acids comprising —SH, —OH, —NH$_2$ or —S—S— groups, thereby forming a permanent bond with the keratin that is resistant to shampooing or cleansing.

The term "water immiscible solvent", as used herein, refers to solvents which cannot be uniformly mixed or blended with water or a separate aqueous phase.

The term "reactive agent", as used herein, refers to compounds that comprise a reactive group or "hook" that is covalently reactive with amino acid based substrates and a monovalent or multivalent cosmetically active functional group that imparts one or more visual, tactile or other cosmetic beneficial effects on proteinaceous materials such as keratin, hair, skin, animal fur or wool.

The term "chemically shelf stable" or "chemically stable", as used herein, applies to a composition comprising a reactive agent wherein the reactive agent does not chemically decompose substantially (via hydrolysis, reduction or oxidation) over the desired shelf life of the product such that the reactive agent maintains its ability to react with the proteinaceous substrate.

The treatment compositions of the present invention can comprise, consist of, or consist essentially of the essential elements and limitations of the invention described herein, as well as any of the additional or optional ingredients, components, or limitations described herein.

All cited references are incorporated herein by reference in their entireties. Citation of any reference is not an admission regarding any determination as to its availability as prior art to the claimed invention.

All percentages, parts and ratios are by weight of the total composition, unless otherwise specified. All such weights as they pertain to listed ingredients are based on the specific ingredient level and, therefore, do not include solvents, carriers, by-products, filler or other minor ingredients that may be included in commercially available materials, unless otherwise specified.

Multiple emulsions are composed of droplets of one liquid dispersed in larger droplets of a second liquid which are in turn dispersed in a final continuous phase. In addition, emulsions typically consist of a continuous phase and a discontinuous phase. For example, in an oil-in-oil-in-water (O/OW) multiple emulsion, the oil-in-oil emulsion is the discontinuous phase and the water phase is the continuous phase.

For an O/O/W system, in which the external continuous phase is aqueous, the primary emulsion is an oil-in-oil emulsion ($O_1/O_2$), which is then emulsified into the external aqueous phase. For the purposes of clarity, and in accordance with recognized standards of nomenclature, the external aqueous phase is designated as (W), and the primary oil-in-oil emulsion is designated as ($O_1/O_2$). The primary oil-in-oil emulsion ($O_1/O_2$) includes an internal oil phase which is designated as ($O_1$) contained within a middle oil phase which is designated as ($O_2$). After the primary emulsion ($O_1/O_2$) has been further dispersed in the external aqueous phase (W), the complete multiple emulsion system is designated as ($O_1/O_2/W$).

A primary advantage of the present invention is the provision of a delivery system approach that will enable the formulation and delivery of reactive agents to amino acid based substrates from an aqueous composition that is chemically shelf stable. This is accomplished via an oil-in-oil-in-water multiple emulsion delivery system ($O_1/O_2/W$), wherein the reactive agent is solubilized within a suitable ($O_1$) oil and then the ($O_1$) phase comprising the reactive agent is emulsified within a suitable ($O_2$) oil to form a primary oil-in-oil emulsion ($O_1/O_2$). The resulting oil-in-oil emulsion is then emulsified within the aqueous continuous phase (W) to form a multiple emulsion ($O_1/O_2/W$), which confers improved chemical shelf stability to the reactive agent. While not intending to be limited by theory, it is believed that the ($O_2$) phase provides a barrier between the ($O_1$) phase and the aqueous continuous phase in order to minimize contact between the chemically unstable reactive agent and the aqueous continuous phase.

In its simplest form, the emulsion treatment compositions of the present invention include (a) an aqueous continuous phase; and (b) a discontinuous phase in the form of an oil-in-oil emulsion which comprises (i) a reactive component including a reactive agent and an internal oil, wherein the internal oil solubilizes the reactive agent, and (ii) a middle oil in which the reactive component is dispersed, wherein the middle oil is immiscible with the internal oil, does not solubilize the reactive agent, is immiscible in the aqueous continuous phase, and includes a hydrophobic particulate thickener.

The oil-in-oil-in-water multiple emulsion treatment compositions of the present invention typically comprise the primary oil-in-oil emulsion ($O_1/O_2$) in an amount which provides the desired shelf stability. In one embodiment, the oil-in-oil-in-water multiple emulsion treatment compositions comprise the primary oil-in-oil emulsion ($O_1/O_2$) in an amount of from about 1% to about 60%, more preferably from about 5% to about 55%, and more preferably still from about 10% to about 50%, based on the weight of the oil-in-oil-in-water multiple emulsion composition.

Discontinuous Phase—Primary Oil-in-Oil Emulsion ($O_1/O_2$).

The discontinuous phase of the emulsion treatment compositions of the present invention includes a reactive component including a reactive agent and an internal oil, and a middle oil in which the reactive component is dispersed and which also comprises a hydrophobic particulate thickener.

Reactive Component

The emulsion treatment compositions of the present invention include a reactive component which in turn comprises a reactive agent and an internal oil which solubilizes the reactive agent.

Reactive Agent

The reactive agent comprises a reactive group or "hook" and a mono or multivalent cosmetically active functional group that imparts one or more visual, tactile or other cosmetic beneficial effects on proteinaceous materials such as keratin, hair, skin, animal fur or wool. The reactive agent comprises one or more reactive groups selected from the group consisting of electrophilic, nucleophilic, protected thiol groups and mixtures thereof.

Disclosed technologies for the covalent attachment of cosmetic actives (primarily dyes and conditioners) to hair keratin have primarily relied upon electrophilic (electron accepting) and nucleophilic (electron donating) reactive groups or "hooks".

Electrophilic reactive groups or "hooks" that may be included within reactive agents of the present inventions include, but are not limited to, the following:

Azlactones as described in U.S. Pat. No. 5,656,265 by P. Bailey et. al., and U.S. Pat. Nos. 5,523,080 and 5,525,332 both by A. Gough et. al.

Alkyl halides as described in U.S. Pat. Nos. 5,211,942 and 5,030,756 by T. Deppert et. al.

Thiosulfates as described in U.S. Pat. No. 3,415,606 by R. Randebrock.

Dithiocarboxylic acid esters wherein preferred carboxyalkyl carbodithioates have the general formula:

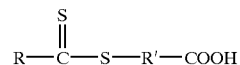

where R is an organic group and
R' is an alkylene group containing 1, 2 or 3 carbon atoms.
The group R may be:
(a) an aliphatic group, for example alkyl, which may contain far instance up to 24 carbon atoms;
(b) an aromatic group, for example phenyl or naphtyl;
(c) a mixed aliphatic-aromatic group for example alkaryl or aralkyl;
(d) a heterocyclic group, for example furyl;
(e) a quaternary ammonium-alkylene group, for example an N-pyridinium-alkylene group,
(f) a chromophoric group, for example, anthraquinonyl, an azo-containing radical, phthalocyaninie; or
(g) any group (a) to (e) containing substituents such as carboxyl, sulphonic acid, halogeno, nitro, oxo, hydroxyl, acylamino, or a further carboxyalkyl carbodithioate group, but not mercapro (—SH) or primary amino (—$NH_2$).

—Acyl halides—polyhaloacetylated polymers are essentially characterized in that they all contain a halogen (chlorine or bromine, but preferably chlorine) on a carbon in the alpha position relative to a carbonyl group. These polymers which are polyhaloacetylated and preferably polychloroacetylated, may be obtained according to different methods. In particular, they may be obtained by the homopolymerization or the copolymerization of a haloacetylated monomer carrying a polymerizable double bond;

among the haloacetylated monomers, there will be mentioned, in particular, the following: vinyl chloroacetate, allyl chloroacetate, vinyl chloroformate, N-allyl chloroacetyl-methyl 2-chloroacetamidoacrylate, N-chloroacetamidomethyl acrylamide, N-chloroacetamidomethyl methacrylamide, 5 2-(chloroacetoxy)propyl methacrylate, 2-(chloroacetylcarbamoyloxy)propyl methacrylate, N-methacryloyl-N'-chloroacetylurea and the like; in the case of a copolymerization, a comonomer which promotes the solubility of the final copolymer in the solvent desired, which is generally water or a water-alcohol mixture, is preferably chosen; among comonomers, there will be mentioned, in particular, the following N-vinylpyrrolidone, N,N-dimethylacrylamide, N-acrylamidomethyl-2-oxopyrrolidone, 3-methacrylamidopropyl-1-(N,N,N-trimethylammonium) chloride, methylacrylate, methylmethacrylate, N,N-dimethylacrylamide and the like. The haloacetylated monomers are known and may be prepared according to known methods. The polyhaloacetylated polymers may also be obtained by attaching a haloacetyl group to a polymer carrying amine or primary or secondary alcohol groups, the haloacetyl group being attached in a known manner which consists in reacting a haloacetyl halide, preferably chloroacetyl chloride, with the said polymer carrying amine or alcohol groups; among the polymers which may be employed for this haloacetylation reaction, there may by mentioned, in particular: polyvinyl amine, polyvinyl alcohol, 2-hydroxyethyl polyacrylate, polylysine, copolymers obtained by condensing 2,2-dimethyl-1,3-diaminopropane with methylene bisacrylamide, water-soluble protein hydrolysates and the like. The polyhaloacetylated polymers employed preferably have a molecular weight generally of between 500 and 50,000. Although some of the homopolymers and copolymers are known, examples for the preparation of some of them as well as examples for the preparation of the haloacetylated monomers will be given as follows: Among the homopolymers and the polyhaloactylated copolymers which are particularly preferred for implementing the method, the following may be mentioned: N-vinylpyrrolidone/vinyl chlchloroacetate copolymer, methyl 2-chloroacetamidoacrylate/N-acrylamido-methyl-2-oxopyrrolidine copolymer, methyl 2-chloroacetamidoacrylate homopolymer, N-chloroacetamidomethyl acrylamide/N-acrylamidomethyl-2-oxopyrrolidine copolymer, methyl 2-chloroacetamidoacrylate/methacrylamido-propyl trimethylammonium chloride copolymer, N-chloroacetamidomethyl acrylamide/methyl acrylate copolymer, N-chloroacetamidomethyl acrylamide homopolymer, and N-chloroacetamidomethyl acrylamide/methacrylamido-propyl trimethylammonium chloride copolymer.

N-ethylmaleimides.

Halotriazines and halopyrimidines as described in U.S. Pat. No. 3,340,000 by A. Shansky.

Vinylsulfones as manufactured by Carbic Hoechst Corporation, (451 Washington Street, New York 13, N.Y.). The structural formula far a typical vinyl sulfone is the following:

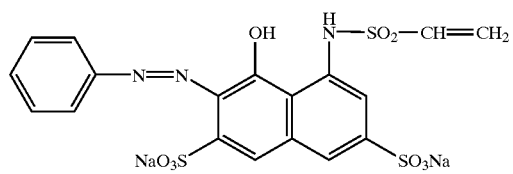

A list of vinyl sulfones includes: Remazol Red (B), Remazol Black (B), Remazol Brilliant Blue (R), Remazol Red-Violet (R), Remazol Yellow (RT) and Remazol Yellow (GN).

Urea derivatives as described in U.S. Pat. No. 3,725,525 by B. Joos.

Alkoxysilanes as described in EP0159628 by R. Stadnick and U.S. Pat. No. 4,567,039 by R. Stadnick et. al.

Isothiuroniums as described in U.S. Pat. Nos. 5,254,335 and 5,206,013 both by T. Deppert et. al.

Monohalotriazines and dihalotriazines, dihaloquinoxaline, dihalopyrimidines, □-haloethylsulfones, □-sulfatoethylsulfones, acrylates, methacrylates, acrylamides, methacrylamides, malemimides, halomaleimides, epoxides, aziridines and derivatives, esters, oxazolinium, imidazolium, thiazolidinium, acid derviatives of carboxylates and sulfates, esters, carbamates, anhydrides, isothiocyanates, isocyanates, lactones, and azlactones having the structure:

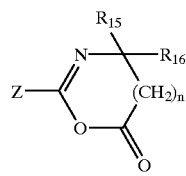

wherein Z represents the remainder of the molecule, $R_{15}$ and $R_{16}$ can be the same or different and are chosen from $C_1$–$C_{12}$ alkyl, $C_2$–$C_{24}$ alkenyl, $C_3$–$C_{12}$ cycloalkyl, $C_5$–$C_{26}$ aryl or $R_{15}$ and $R_{16}$ can form a carbocyclic containing 4 to 12 atoms and further wherein any $R_{15}$ and $R_{16}$ can contain 0 to 3 heteroatoms chosen from S, N, and O.

Nucleophilic reactive groups or "hooks" that may be included within reactive agents of the present inventions include, but are not limited to, the following:

Thiols or thiolates as described in U.S. Pat. No. 3,484,417 by G. Kalopissis et. al., U.S. Pat. Nos. 5,935,560 and 5,935,560, both by J. Seper et. al., and U.S. Pat. No. 5,776,454 by R. Gee et. al., all incorporated herein by reference.

Thiols or thiolates containing quaternary salts as described in U.S. Pat. No. 4,973,475 by R. Schnetzinger et. al., U.S. Pat. Nos. 5,087,733 and 5,206,013 both by T. Deppert et. al.

Thioalkylamides as described in U.S. Pat. No. 5,068,378 by D. Halloran et. al.

Thioalkyl esters as described in U.S. Pat. No. 5,350,572 by A. Savaides et. al.

Cysteamine derivatives having the formula:

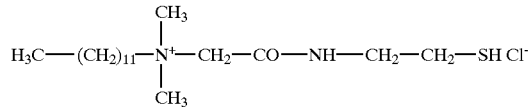

wherein the above formula is N-dodecyl-N,N-dimethyl glycine cysteamine hydrochloride, also known as N-dodecyl amino betaine mercaptoethylamine (DABM).

Protected thiol reactive groups or "hooks" that may be included within reactive agents of the present inventions include, but are not limited to, reactive groups of the following structure:

$$R-(S-Pr)_m$$

where R is a mono or multivalent cosmetically active functional group, S is sulfur, Pr is a protecting group and m is an integer between 1 and 100. The protecting group is selected from the group consisting of heterocyclic protecting groups, $sp^2$ aliphatic trigonal carbon protecting groups, $sp^3$ carbon electrophilic protecting groups, phosphorus protecting groups, metal based protecting groups, non-metal and metalloid based protecting groups, energy-sensitive protecting groups and mixtures thereof as described in U.S. Pat. No. 6,544,499 and U.S. patent application Ser. No. 09/227,912, both by R. Glenn et. al.

Preferred reactive groups or "hooks" of the present invention include those of the protected thiol type. Of the thiol protective groups, the heterocyclic protecting groups, the $sp^2$ protecting groups and the phosphorus protecting groups are preferred, with the heterocyclic protecting groups being more preferred. Of the heterocyclic protecting groups, the pyrimidinium, pyridinium, and benzothiazolium classes are preferred, with the pyrimidinium class being more preferred.

The mono or multivalent cosmetically active functional group, R, suitable for inclusion within the reactive agents of the present invention may be any moiety that imparts one or more visual, tactile or other cosmetic beneficial effects on proteinaceous materials such as keratin, hair, skin, animal fur or wool. Any cosmetic moiety may be included as a functional group in the compositions of the present invention as long as the compound can be modified to contain at least one reactive group or "hook" as described herein and in the references provided herein.

Suitable functional groups that are suitable for inclusion within the reactive agents of the present invention include, but are not limited to, antimicrobial compounds, UV-absorbing compounds, skin conditioning agents, hair conditioning agents, hair repair agents, hair styling agents, hair dyes, scalp treatment agents, anti-inflammatory compounds, antioxidants, dyes and coloring agents, perfumes, oral care actives, skin moisturizers, pharmaceutical agents, antidandruff agents, insect repellents, moisturizers, humectants, pearlescent and/or opacifying materials, fabric care actives, pet grooming actives, fabric anti-wrinkling agents, shrink-resistant actives, laundry care actives, hard surfaces actives, textile actives, textile dyes, water-proofing agents, cationic polymers, cationic surface modifiers, hydrophobic surface modifiers, anionic surface modifiers, absorbents, antifungal agents, insecticidal agents, textile color guards, nail actives such as enamel and polish, eyelash actives and mascara, antiperspirant and deodorant actives, anti-acne actives, odor control actives, fluorescent actives, bleaching agents, enzymes, antibodies, dispersing aids, emollients, stabilizers, anti-static agents, antiseborrhea agents, optical brighteners, fluorescent dyes, softeners, cross-linking agents, photobleaches, bactericides, and mixtures thereof. A more detailed listing of cosmetic functional groups is set forth in U.S. Ser. No. 09/478,855 by R. Glenn et. al.

Preferred cosmetic functional groups include hair conditioning agents, hair repair agents, hair styling agents, and hair dyes and coloring agents. Please see U.S. Ser. No. 09/478,855 by R. Glenn et. al. for a more thorough list of preferred cosmetic functional groups.

An exemplary reactive agent to demonstrate the present invention comprises a protected thiol reactive group of the pyrimidinium type combined with a silicone hair conditioning cosmetic functional group. The structure of this exemplary reactive agent is as follows:

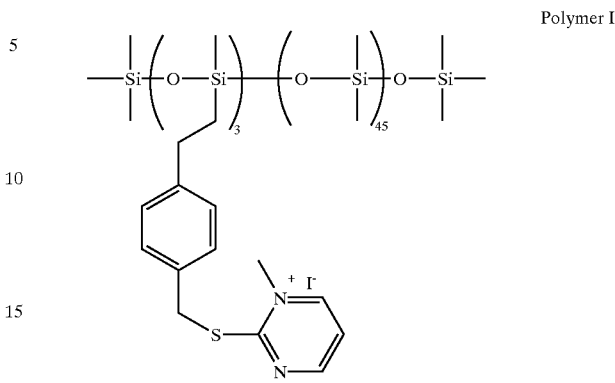

Polymer I

This compound and its synthesis preparation are disclosed within U.S. Ser. No. 09/478,855 by R. Glenn et. al. Additional reactive agents containing a silicone hair conditioning cosmetic functional group are be found within U.S. application Ser. No. 09/616,535 by M. Butts et al., filed Jul. 14, 2000, U.S. application Ser. No. 09/616,534 by M. Butts et al., filed Jul. 14, 2000, U.S. application Ser. No. 09/616,533 by M. Butts et al., filed Jul. 14, 2000, U.S. application Ser. No. 09/616,532 by M. Butts et al., filed Jul. 14, 2000, all of which are incorporated by reference herein. Polymer I is chemically shelf unstable with the pyrimidinium moiety being prone to premature hydrolysis in the presence of aqueous media.

An additional exemplary reactive agent to demonstrate the present invention comprises an electrophilic reactive group of the azlactone type combined with a silicone hair conditioning cosmetic functional group. The structure of this exemplary reactive agent is as follows:

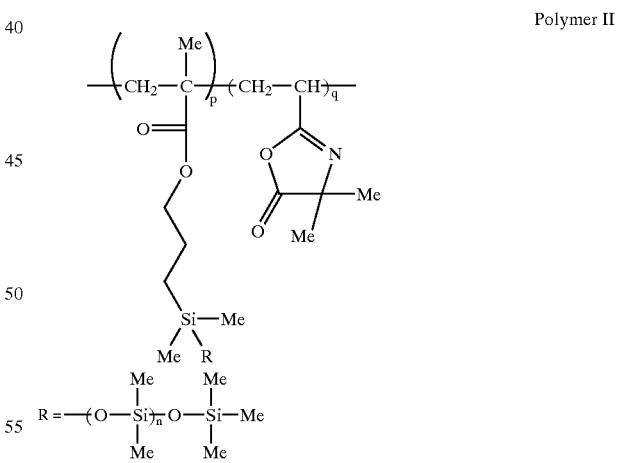

Polymer II where p=1, q=14.6 and n=60. This compound and its synthesis preparation is disclosed within U.S. Pat. No. 5,525,332 by A. D. Gough et. al. from column 12, lines 11–67 through Column 13, lines 1–18.

An additional exemplary reactive agent to demonstrate the present invention comprises a nucleophilic reactive group of the thiol type combined with a hydrocarbon conditioning cosmetic functional group. The structure of this exemplary reactive agent is as follows:

Polymer (Conditioner) III

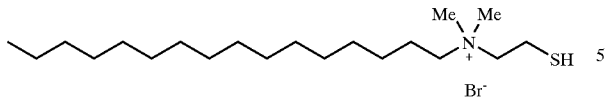

This compound and its synthesis preparation is disclosed within U.S. Pat. No. 5,087,733 by T. M. Deppert et. al. from column 6, lines 35–68 and Column 7, lines 10–15.

The emulsion treatment compositions typically comprise the reactive agent in an amount of from about 0.01% to about 10%, more specifically from about 0.5% to about 8%, and more specifically still from about 1% to about 5%, based on the weight of the emulsion treatment composition ($O_1/O_2/W$).

($O_1$) Phase

The discontinuous phase of the oil-in-oil emulsion employed in the treatment compositions of the present invention also comprises an oil ($O_1$). The oil ($O_1$) helps to solubilize or disperse the reactive agents described hereinbefore. While it is recognized that some components of the composition may be dispersed rather than solubilized in the discontinuous phase, the nomenclature ($O_1$) is employed to describe this component herein. The oil ($O_1$) may comprise either an oil or solvent (both polar and non-polar) provided that the selected reactive agent is sufficiently soluble/dispersible in the selected oil or solvent. Suitable non-polar oils/solvents have a solubility parameter ranging from about 5.5 $(cal/cm^3)^{0.5}$ to about 8.0 $(cal/cm^3)^{0.5}$. Suitable polar oils/solvents have a solubility parameter ranging from about 8.9 $(cal/cm^3)^{0.5}$ to about 15.0 $(cal/cm^3)^{0.5}$. Solubility parameters for the ($O_1$) phase, and means for determining such parameters, are well known in the chemical arts. More specifically, as used herein, the solubility parameter refers to the Vaughan Solubility Parameter (VSP) ($\square$) which is a calculated parameter used to define a material's solubility and is defined as the sum of all the cohesive forces and the square root of the energy of vaporization. The VSP typically has a range of 5–25. A further description of solubility parameters and means for determining them are described by C. D. Vaughan, "Solubility Effects in Product, Package, Penetration and Preservation" 103 *Cosmetics and Toiletries* 47–69, October 1988; and C. D. Vaughn, "Using Solubility Parameters in Cosmetics Formulation", 36 *J. Soc. Cosmetic Chemists* 319–333, September/October, 1988.

Suitable non-polar oils/solvents for the ($O_1$) phase of the emulsion treatment compositions of the present invention include, but are not limited to, volatile or nonvolatile silicone compounds, volatile or nonvolatile hydrocarbon compounds, and mixtures thereof. The volatile silicone compounds can be a linear or cyclic polydimethylsiloxane, such as hexamethylsiloxane or a cyclomethicone, available commercially under the trade names such as DOW CORNING 200 FLUID, DOW CORNING 244 FLUID, DOW CORNING 245 FLUID, DOW CORNING 344 FLUID, and DOW CORNING 345 FLUID from Dow Corning Corporation, Midland, Mich., and SILICONE SF-1173 and SILICONE SF-1202 from General Electric, Waterford, N.Y.

Volatile hydrocarbon compounds include hydrocarbons having about 10 to about 30 carbon atoms, for example, isododecane and isohexadecane, i.e., PERMETHYL 99A, PERMETHYL 101A, and PERMETHYL 102A, available from Presperse, Inc., South Plainfield, N.J.. The volatile hydrocarbon compounds can also include aliphatic hydrocarbons having about 12 to about 24 carbon atoms, and having a boiling point of about 90° C. to about 250° C., i.e., ISOPAR C, ISOPAR E, ISOPAR G, and ISOPAR M, available from Exxon Chemical Co., Baytown, Tex. Other exemplary volatile hydrocarbon compounds are depicted in general structure (I):

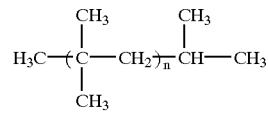

where n ranges from 2 to 5.

Nonvolatile hydrocarbon compounds include mineral oil, a phenyltrimethicone, or branched hydrocarbons according to structure I where n is 5–250 including PERMETHYL 104A, PERMETHYL 106A, and PERMETHYL 108A, available from Presperse, Inc., South Plainfield, N.J.

Nonvolatile silicone compounds include polydimethylsiloxanes having a viscosity at 25° C. of about 6 to about 400 centistokes, such as DOW CORNING 556 FLUID, or DOW CORNING 200 FLUID, respectively, available from Dow Corning Corp., Midland, Mich.

Exemplary, but non-limiting, non-polar oils/solvents for the ($O_1$) phase of the emulsion treatment compositions of the present invention are: cyclomethicone D5 (5.77 VSP), dimethicone (5.92 VSP), cyclomethicone D4 (5.99 VSP), hexamethyldisiloxane (6.15 VSP), neopentane (6.38 VSP), isopentane (6.82 VSP), docosane—C22 (6.6 VSP), nonacosane—C29 (6.83 VSP), C8—isoparaffin (6.93 VSP), white mineral oil (7.09 VSP), pentane (7.1 VSP), tricosane—C22 (7.13 VSP), hexane (7.28 VSP), octadecane (7.29 VSP), eicosane—C20 (7.32 VSP), petrolatum (7.33 VSP), cetane—C16 (7.41 VSP), heptane (7.41 VSP), tridecane—C13 (7.48 VSP), octane (7.58 VSP), dodecane (7.59 VSP), and decane (7.62 VSP).

Preferred non-polar oils/solvents for the ($O_1$) phase of the emulsion treatment compositions of the present invention include volatile hydrocarbon compounds having about 12 to about 24 carbon atoms, and having a boiling point of about 90° C. to about 250° C., e.g., ISOPAR C, ISOPAR E, ISOPAR G, and ISOPAR M, available from Exxon Chemical Co., Baytown, Tex.; and volatile silicone compounds such as hexamethylsiloxane or a cyclomethicone, available commercially under the trade names such as DOW CORNING 200 FLUID, DOW CORNING 244 FLUID, DOW CORNING 245 FLUID, DOW CORNING 344 FLUID, and DOW CORNING 345 FLUID from Dow Corning Corporation, Midland, Mich., and SILICONE SF-1173 and SILICONE SF-1202 from General Electric, Waterford, N.Y.

Suitable polar oils/solvents for the ($O_1$) phase of the emulsion treatment compositions of the present invention include, but are not limited to, amides, esters, ethers, ketones, cyclic amides, cyclic esters, cyclic ketones, cyclic ethers, and mixtures thereof. Nonlimiting examples of such solvents include ethyl formate, dimethyl isosorbide, acetylacetone, 2-butanone, acetone, methyl acetate, ethyl acetate, propyl acetate, ethoxyethanol, dipropylene glycol monomethyl ether, butyl lactate, t-butyl alcohol, phenyl acetate, 2-propoxyethanol, isopropoxyethanol, methoxypropanol, isopropyl lactate, hexyl alcohol, butoxyethanol, tripropylene glycol (PPG-3), triacetin, methoxyethanol, isopropyl alcohol, PEG-8, methyl lactate, PEG-6, PEG-5, PEG-4, N-methylpyrrolidone, propyl alcohol, dipropylene glycol (PPG-2), acetonitrile, phenoxyethanol, triethylene glycol, hexylene glycol, ethyl alcohol, $\square$-butyrolactone, butylene glycol, propylene carbonate, dimethyl sulfoxide, diethylene glycol, ethoxydiglycol, propylene glycol, pyrrolidone, pyrrolidone-2, methyl alcohol, ethylene carbonate, ethylene glycol, acetamide, glycerin, butyl carbitol, 1,3-dioxolane, dimethoxymethane, 1,2-hexanediol, dipropylene glycol butyl ether, dipropylene glycol t-butyl ether, propionaldehyde, diethoxymethane and glycerol formal.

Exemplary, but non-limiting, polar oils/solvents for the ($O_1$) phase of the emulsion treatment compositions of the present invention are: butyl acetate (8.93 VSP), ethyl formate (9.55 VSP), dimethyl isosorbide (9.58 VSP), acetylacetone (9.68 VSP), 2-butanone (9.8 VSP), acetone (9.87 VSP), methyl acetate (9.88 VSP), ethoxyethanol (9.9 VSP), dipropylene glycol monomethyl ether (9.99 VSP), butyl lactate (10.27 VSP), t-butyl alcohol (10.28 VSP), phenyl acetate (10.33 VSP), methoxypropanol (10.4 VSP), isopropyl lactate (10.42 VSP), hexyl alcohol (10.5 VSP), butoxyethanol (10.53 VSP), tripropylene glycol—PPG-3 (10.6 VSP), triacetin (10.77 VSP), methoxyethanol (10.8 VSP), isopropyl alcohol (11.24 VSP), PEG-8 (11.34 VSP), methyl lactate (11.47 VSP), PEG-6 (11.47 VSP), PEG-5 (11.57 VSP), PEG-4 (11.61 VSP), N-methylpyrrolidone (11.71 VSP), propyl alcohol (11.73 VSP), dipropylene glycol—PPG-2 (11.78 VSP), acetonitrile (11.81 VSP), phenoxyethanol (11.87 VSP), triethylene glycol (12.21 VSP), hexylene glycol (12.32 VSP), ethyl alcohol (12.55 VSP), gamma-butyrolactone (12.85 VSP), butylene glycol (13.2 VSP), propylene carbonate (13.35 VSP), dimethyl sulfoxide (13.4 VSP), diethylene glycol (13.61 VSP), ethoxydiglycol (13.8 VSP), propylene glycol (14.0 VSP), pyrrolidone (14.0 VSP), pyrrolidone-2 (14.22 VSP), methyl alcohol (14.33 VSP), ethylene carbonate (14.45 VSP), ethylene glycol (14.5 VSP), acetamide (16.03 VSP), and glycerin (16.26 VSP).

Preferred polar oils/solvents for the ($O_1$) phase of the emulsion treatment compositions of the present invention include

- ethoxyethanol available commercially as CELLOSOLVE Solvent from Union Carbide Corporation,
- propylene glycol available commercially as 1,2-Propylene Glycol USP from BASF Corporation or Eastman Propylene Glycol from Eastman Chemical Company; and dipropylene glycol available commercially as Eastman Dipropylene Glycol from Eastman Chemical Company, and ethoxydiglycol available commercially as Eastman DE Solvent from Eastman Chemical Company;
- propylene carbonate, available commercially as ARCONATE PROPYLENE CARBONATE, available from ARCO Chemical Company; and
- hydrofluoroethers, available commercially as HFE-7100, HFE-71DE, HFE-71DA, HFE-71IPA, and HFE-7200, available from 3M Chemicals.

The emulsion treatment compositions typically comprise ($O_1$) in an amount of from about 1% to about 95%, more preferably from about 10% to about 80%, and more preferably still from about 25% to about 60%, based on the weight of the primary oil-in-oil emulsion.

Oil Phase ($O_2$)

The discontinuous phase of the emulsion treatment compositions of the present invention include an oil phase ($O_2$) which emulsifies or disperses the reactive component to create the primary oil-in-oil emulsion ($O_1/O_2$). It is believed that the oil phase ($O_2$) serves as a barrier between the ($O_1$) phase and the aqueous continuous phase to minimize contact between the chemically unstable reactive agent and the aqueous continuous phase. The barrier also serves to prevent the premature degradation of the reactive agent over the shelf life of the composition to enable the delivery of the reactive agent to the amino acid based substrate, i.e., hair, in a consumer preferable medium, i.e., an aqueous emulsion cream.

Oil Phase ($O_2$) Oils

Preferred ($O_2$) oils suitable for use in the present invention include those oils that are immiscible with the ($O_1$) phase, do not solubilize the reactive agent, and are immiscible in the aqueous continuous phase (W). Preferably, the oil phase ($O_2$) has a solubility parameter ranging from about 6.0 $(cal/cm^3)^{0.5}$ to about 9.0 $(cal/cm^3)^{0.5}$.

Suitable oils for the oil phase ($O_2$) of the emulsion treatment compositions of the present invention include, but are not limited to fatty acid derivatives, di- and tri-glycerides, vegetable oils, vegetable oil derivatives, and liquid nondigestible oils as those described in U.S. Pat. No. 3,600,186 to Mattson, and U.S. Pat. Nos. 4,005,195 and 4,005,196 to Jandacek et. al; blends of liquid digestible or nondigestible oils with solid polyol polyesters as those described in U.S. Pat. No. 4,797,300 to Jandacek, and U.S. Pat. Nos. 5,306,514, 5,306,516, and 5,306,515 to Letton, and acetoglyceride esters, alkyl esters, alkenyl esters, lanolin and its derivatives, milk tri-glycerides, wax esters, beeswax derivatives, sterols, phospholipids, hydroxylated milk glyceride, beeswax, spermaceti, myristyl myristate, stearyl stearate, carnuba and candelilla waxes, cholesterol fatty acid esters and homologs thereof, $C_6$–$C_{18}$ N-alkyl pyrrolidones, $C_6$–$C_{18}$ alkyl carbonates, lecithin and derivatives, sphingo lipids, ceramides, glycosphingo lipids and homologs thereof and mixtures thereof.

Exemplary di- and tri-glyceride oils include castor oil, soybean oil, derivatized soybean oils such as maleated soy bean oil, safflower oil, cotton seed oil, corn oil, walnut oil, peanut oil, olive oil, cod liver oil, almond oil, avocado oil, palm oil, sesame seed oil, vegetable oils and vegetable oil derivatives, coconut oil and derivatized coconut oil, cottonseed oil and derivatized cottonseed oil, jojoba oil, cocoa butter, and mixtures thereof.

Liquid nondigestible oils include polyol polyesters such as sucrose polyesters, for example cottonseed sucrose octaesters, and solid polyol polyesters include sucrose octaesters prepared from $C_{22}$ fatty acids. Specific examples of liquid nondigestible oils include a mixture of esters of behenic acid and sucrose available commercially as SEFA Behenate from The Procter & Gamble Company Cincinnati, Ohio, and a mixture of esters of cottonseed acid and sucrose available commercially as SEFA Soyate/Cottonate from The Procter & Gamble Company Cincinnati, Ohio.

Ester oils include those comprising an aliphatic alcohol hating about eight to about twenty carbon atoms, and an aliphatic or aromatic carboxylic acid including from two to about twelve carbon atoms, or conversely, an aliphatic alcohol having two to about twelve carbon atoms with an aliphatic or aromatic carboxylic acid including about eight to about twenty carbon atoms. The ester is either straight-chained or branched. Preferably, the ester has a molecular weight of less than about 500. Nonlimiting examples of suitable esters include, but are not limited to, a) aliphatic monohydric alcohol esters, including, but not limited to, myristyl propionate, isopropyl isostearate, isopropyl myristate, isopropyl palmitate, cetyl acetate, cetyl propionate, cetyl stearate, isodecyl neopentonoate, cetyl octanoate, and isocetyl stearate; b) aliphatic di- and tri-esters of polycarboxylic acids, including, but not limited to, diisopropyl adipate, diisostearyl fumarate, dioctyl adipate, and triisostearyl citrate; c) aliphatic polyhydric alcohol esters, including, but not limited to, propylene glycol dipelargonate; and d) aliphatic esters of aromatic acids, including, but not limited to $C_{12}$–$C_{15}$ alcohol esters of benzoic acid, octyl salicylate, sucrose benzoate, and dioctyl phthalate. Additional esters are listed in the International Cosmetic Ingredient Dictionary and Handbook, Vol. 2, Eight Ed., The Cosmetic Toiletry and Fragrance Assn., Inc., Washington, D.C. (2000) at pages 1670 through 1676, incorporated herein by reference.

The acetoglyceride esters include acetylated monoglycerides and the lanolin and its derivatives include lanolin, lanolin oil, lanolin wax, lanolin alcohols, lanolin fatty acids, isopropyl lanolate, acetylated lanolin, acetylated lanolin alcohols, lanolin alcohol linoleate, and lanolin alcohol riconoleate.

Preferred oils for the oil phase ($O_2$) of the emulsion treatment compositions of the present invention include:

Vegetable oils including soybean oil available commercially as Cropure Soybean from Croda Oleochemicals, North Humberside, England; castor oil available commercially as Castor Oil USP from United Catalysts, Louisville, Ky.; and coconut oil available commercially as Cropure Coconut from Croda Oleochemicals, North Humberside, England;

Liquid non-digestible oils and mixtures of liquid non-digestible oils with solid polyol polyesters including a mixture of esters of behenic acid and sucrose available commercially as SEFA Behenate from The Procter & Gamble Company Cincinnati, Ohio, and a mixture of esters of cottonseed acid and sucrose available commercially as SEFA Soyate/Cottonate from The Procter & Gamble Company Cincinnati, Ohio; and Aliphatic esters including isopropyl myristate available commercially as Crodamol IPM from Croda Oleochemicals, North Humberside, England.

The emulsion treatment compositions typically comprise the oil phase ($O_2$) in an amount of from about 1% to about 95%, more preferably from about 25% to about 80%, and more preferably still from about 40% to about 60%, based on the weight of the primary oil-in-oil emulsion.

Oil Phase ($O_2$) Particulate Thickener

The oil phase ($O_2$) of the emulsion treatment compositions of the present invention also includes a particulate thickener. While not intending to be limited by theory, it is believed that the addition of a particulate thickener to the oil phase ($O_2$) serves as a further barrier between the reactive agent and the aqueous continuous phase and also serves to prevent coalescence of the ($O_1$) phase. It is further believed that the particulate thickener functions to impart a yield point to the ($O_2$) oil which mitigates Brownian movement within the oil phase ($O_2$). It is also believed that the steric stabilization afforded by the particulate thickener coupled with the resulting higher viscosity acts to prevent coalescence of the ($O_1$) phase, thereby imparting phase stability to the primary emulsion ($O_1/O_2$).

Preferred particulate thickeners suitable for use in the present invention include those thickeners that are immiscible in the aqueous continuous phase (W) and can take the form of a wax, hydrophobic silica, hydrophobic clay or mixtures thereof.

In one embodiment of the present invention, the particulate thickener can comprise a crystalline, hydroxyl-containing stabilizer. The crystalline, hydroxy-containing stabilizer is selected from the group consisting of:

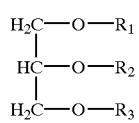
(i)

wherein $R_1$ is

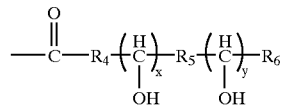

$R_2$ is $R_1$ or H, $R_3$ is $R_1$ or H, $R_4$ is a single bond or $C_{1-20}$ alkyl, $R_5$ is a single bond or $C_{1-20}$ alkyl, $R_6$ is H or $C_{1-20}$ alkyl, and $R_4+R_5+R_6=C_{1-22}$, and wherein $1 \leq x+y \leq 4$;

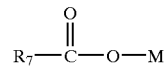
(ii)

wherein $R_7$ is —$R_4(CHOH)_xR_5(CHOH)_yR_6$, wherein $R_4$, $R_5$, $R_6$, x and y are as defined above; and M is $Na^+$, $K^+$, $Mg^{++}$, or H; and iii) mixtures thereof.

Some preferred hydroxyl-containing stabilizers include 12-hydroxystearic acid, 9,10-dihydroxystearic acid, tri-9,10-dihydroxystearin and tri-12-hydroxystearin (hydrogenated castor oil is mostly tri-12-hydroxystearin). Tri-12-hydroxystearin is most preferred for use in the emulsion compositions herein. Tri-12-hydroxystearin is available commercially as Thixcin R® from Rheox and as Flowtone® from Southern Clay Products.

In another embodiment of the present invention, the particulate thickener can comprise hydrophobically modified dispersed amorphous silica. As used herein the term "dispersed amorphous silica" refers to small, finely divided non-crystalline silica having a mean agglomerate particle size of less than about 100 microns.

Fumed silica, which is also known as arced silica, is produced by the vapor phase hydrolysis of silicon tetrachloride in a hydrogen oxygen flame. It is believed that the combustion process creates silicone dioxide molecules which condense to form particles. The particles collide, attach and sinter together. The result of this process is a three-dimensional branched chain aggregate. Once the aggregate cools below the fusion point of silica, which is about 1710□C., further collisions result in mechanical entanglement of the chains to form agglomerates. Precipitated silicas and silica gels are generally made in aqueous solution. See, Cabot Technical Data Pamphlet TD-100 entitled "CAB-O-SIL® Untreated Fumed Silica Properties and Functions", October 1993, and Cabot Technical Data Pamphlet TD-104 entitled "CAB-O-SIL® Fumed Silica in Cosmetic and Personal Care Products", March 1992, both of which are herein incorporated herein by reference.

The fumed silica preferably has a mean agglomerate particle size ranging from about 0.1 microns to about 100 microns, more preferably from about 1 micron to about 50 microns, and more preferably still from about 10 microns to about 30 microns. The agglomerates are composed of aggregates which have a mean particle size ranging from about 0.01 microns to about 15 microns, preferably from about 0.05 microns to about 10 microns, more preferably from about 0.1 microns to about 5 microns and more preferably still from about 0.2 microns to about 0.3 microns. The silica preferably has a surface area greater than 50 sq. m/gram, more preferably greater than about 130 sq. m./gram, and more preferably still greater than about 180 sq. m./gram.

The fumed silica is hydrophobically modified via the addition of non-polar moieties to the surface of the silica. Exemplary hydrophobically modified fumed silicas for use in the present invention include, but are not limited to, silica dimethyl silylate whereby the fumed silica's surface has been modified with dimethyl silyl groups available commercially as Aerosil R972 and Aerosil R974 both available from Degussa; and CAB-O-SIL TS-610 and CAB-O-SIL TS-720 both available from Cabot; and silica silylate whereby the fumed silica's surface has been modified with trimethylsiloxyl groups available commercially as Aerosil R812 and Sipernat D17 both available from Degussa; and CAB-O-SIL TS-530 available from Cabot.

In another embodiment of the present invention, the particulate thickener can comprise hydrophobically modified dispersed smectite clay selected from the group consisting of bentonite, hectorite and mixtures thereof. Bentonite is a colloidal aluminum clay sulfate. See Merck Index, Eleventh Edition, 1989, entry 1062, p. 164. Hectorite is a clay containing sodium, magnesium, lithium, silicon, oxygen, hydrogen and fluorine. See Merck Index, Eleventh Edition, 1989, entry 4538, p. 729.

Hyrophobically modified dispersed smectite clays are called organoclays and are formed by reacting monoquaternary compounds with the smectite clays to form an organoclay complex. Non-limiting examples of organoclays for use in the present invention include dihydrogenated tallow benzylmonium hectorite available commercially as Bentone SD-3 from Rheox; quaternium-18 hectorite available commercially as Bentone 38 and in mixtures M-P-A 14, Bentone Gel DOA, Bentone Gel ECO 5, Bentone Gel EUG, Bentone Gel IPP, Bentone Gel ISD, Bentone Gel MIO, Bentone Gel MIO-A40, Bentone Gel SS-71, Bentone Gel 10ST, Bentone Gel VS-5, Bentone Gel VS-8, Bentone Gel VS-38, Bentone Gel VS-5PC, and Bentone Gel YVS all available from Rheox; quaternium-18 bentonite available commercially as Bentone 34 from Rheox and Claytone 40 and Claytone SO from Southern Clay; quaternium-18/benzalkonium bentonite available commercially as Claytone HT from Southern Clay; stearalkonium bentonite available commercially as Claytone AF from Southern Clay, Toxogel LG and Tixogel VZ from United Catalysts, and Viscogel B7 from Bentec; and stearalkonium hectorite available commercially as Bentone 27 from Rheox and in mixtures Bentone Gel CAO, Bentone Gel IPM, Bentone Gel LOI, Bentone Gel M-20, Bentone Gel RSS, Bentone Gel SIL, and Bentone Gel TN, all from Rheox.

The emulsion treatment compositions typically comprise the particulate thickeners in an amount of from about 1% to about 30%, more preferably from about 3% to about 20%, and more preferably still from about 5% to about 15%, based on the weight of the oil phase ($O_2$).

Primary Emulsion ($O_1/O_2$) Emulsifier (e1)

The hereinbefore described primary oil-in-oil emulsion ($O_1/O_2$) of the emulsion treatment compositions of the present invention may further comprise an optional surface active emulsifier (e1) to facilitate the formation of the primary oil-in-oil emulsion ($O_1/O_2$). More particularly, the emulsifier (e1) is comprised of two parts, (A) and (B), where (A) is soluble in ($O_1$) and (B) is soluble in ($O_2$). Such an optional emulsifier (e1) can take the form of either a polymeric surfactant or an amphiphilic surfactant. Polymeric surfactants suitable for use herein take the form of a block copolymer, e.g. A-B-A or B-A-B or A-$(B-A)_n$-B-A or B-$(A-B)_n$-A-B, or a graft polymer with pendant side chains, e.g., A-$(A)_m$-$(A(B))_n$-A or B-$(B)_m$-$(B(A))_n$-B, where m is 0 to 1000 and n is 1 to 1000. Amphiphilic surfactants suitable for use herein take the form of A-B that preferably adsorbs at the ($O_1/O_2$) interface.

The choice of (A) depends on ($O_1$). For example, if ($O_1$) is a hydrocarbon, then (A) can be an alkyl, branched alkyl, alkenyl, or branched alkenyl moiety with 3 to 30 carbons; if ($O_1$) is a dimethicone or silicone, then (A) can be a poly-dimethylsiloxane (PDMS) moiety with between 4 to 500 PDMS units; and if ($O_1$) is an oxygenated solvent such as ethylene glycol, then (A) can be a polyalkylene oxide moiety, i.e., polyoxyethylene. Similarly, the choice of (B) depends on the type of ($O_2$) oil. For example, if ($O_2$) is a triglyceride, then (B) can be a polyalkylene oxide moiety, i.e., polyethylene oxide, polypropylene oxide, and polybutylene oxide, with 1 to 100 alkylene oxide units. Similarly, if ($O_2$) is a sucrose polyester, then (B) can be a polysaccharide moiety. These are exemplary embodiments only, and one skilled in the art will appreciate that there are numerous other combinations of oils suitable for use in the present invention.

Optional emulsifier (e1) for use in combination with the primary emulsion ($O_1/O_2$) defined herein includes any combination of (A)'s and (B)'s in either the polymeric surfactant or the amphiphilic surfactant form wherein (A) and/or (B) can comprise, but are not limited to, alkyl, alkenyl, branched alkyl, branched alkenyl, polydimethylsiloxane, alkylene oxide, cellulosic, polysaccharide, polyacrylate, or polystyrene.

Specific nonlimiting examples of suitable emulsifiers (e1) include propylene glycol alginate available commercially as Kelcoloid LVF from Kelco; cetyl hydroxyethylcellulose available commercially as Natrasol Plus from Aqualon; nonoxynol hydroxyethylcellulose available commercially as Amercell Polymer HM-1500 from Amerchol; acrylate/carboxyvinyl copolymer available commercially as Rheolate 5000 from Rheox; $C_{10-30}$ alkyl modified acrylate crosspolymer available commercially as Carbopol 1342 and 1382 from BF Goodrich; acrylate/acrylonitrogen copolymer available commercially as Hypan Hydrogel SA100H from Lipo Chemicals, Inc., Paterson, N.J.; acrylate/steareth-20 methacrylate copolymer available commercially as Aculyn 22 from Rohm and Haas; ethylene/acrylic acid copolymer available commercially as A–C grades 143, 540, 580 from Allied-Signal; ethylene/vinyl acetate copolymer available commercially as A–C grades 400, 403, 430 from Allied-Signal; PEG-n stearates and PEG-n distearates including PEG-8 stearate, PEG-8 distearate, and PEG-40 stearate available commercially as Emerest 2711, 2712 & 2715 from Henkel, and PEG-12 mono- and di-stearate and PEG-150 distearate available commercially as Mapeg 600MS, 600DS and 6000DS from PPG-Mazer, and PEG-200 to 6000 mono- and di-stearate available commercially within the Kessco line from Stepan; ethylene oxide/propylene oxide block poloxamer copolymers available commercially as Symponic PF127 from ICI and within the Pluracare line from BASF; PEG-120 methyl glucose dioleate available commercially as Glucamate DOE-120 from Amerchol; methyl vinyl ether/maleic anhydride crosspolymer available commercially as Stabileze 06 from International Specialty Polymer; polyhydroxystearic acid/polyethylene oxide copolymers available commercially as Arlacil P135 from Unichem; dimethicone copolyols available commercially as DOW CORNING 3225C FORMULATION AID from Dow Corning Co.; alkyl dimethicone copolyols such as cetyl dimethicone copolyol available commercially as ABIL EM90 from Goldschmidt Chemical Corporation; polyoxyalkylene block copolymers including Poloxamer 101, Poloxamer 105, PPG-2-Buteth-3, PPG-3-Buteth-5, PPG-5-Buteth-7, PPG-7-Buteth-10, PPG-9-Buteth-12, PPG-12-Buteth-16, PPG-15-Buteth-16, PPG-15-Buteth-20, PPG-20-Buteth-30, PPG-24-Buteth-27, PPG-28-Buteth-35, and PEG-15 Butanediol; and polyoxamines, i.e., polyoxyethylene-polyoxypropylene block copolymers of ethylene diamine.

When an optional emulsifier (e1) is used in the primary emulsion herein, it is typically included in an amount of from about 0% to about 20%, more preferably from about 0.1% to about 15%, and more preferably still from about 0.1% to about 12%, based on the weight of the primary oil-in-oil emulsion.

External Aqueous Continuous Phase

The external aqueous continuous phase (W) of the emulsion treatment compositions of the present invention comprises water as a primary ingredient. Aqueous organic solvents may also be included, provided that they do not destabilize the primary oil-in-oil emulsion ($O_1/O_2$). The total concentration of the external aqueous continuous phase (W) in the emulsion treatment compositions of the present invention ranges from about 40% to about 99%, more preferably from about 45% to about 90%, and more preferably still from about 50% to about 85%, based on the weight of the emulsion treatment compositions.

The continuous phase of the emulsion treatment compositions of the present invention may further comprise an emulsifier (e2) to facilitate the formation of the multiple emulsion ($O_1/O_2/W$). Emulsifiers (e2) for use in the external aqueous continuous phase of the present emulsion treatment compositions may include an anionic surfactant, cationic surfactant, amphoteric surfactant, water-soluble polymeric surfactant, water-soluble silicone-containing surfactant, nonionic surfactant having an HLB of greater than about 10, or a surfactant system capable of forming stabilizing liquid crystals around the $O_1/O_2$ droplets. The nonionic surfactant preferably has an HLB of at least 12, and more preferably, an HLB value of at least about 15.

The HLB value, or hydrophilic-lipophilic-balance value, of a surfactant is a well known term to those skilled in the art. The HLB value is related to the solubility of the surfactant, wherein a surfactant with a low HLB value, e.g., about 10 or less, tends to be oil soluble and a surfactant with a high HLB value, e.g., greater than about 10, tends to be water soluble.

The emulsifier for the external phase does not gel the external aqueous phase. The emulsifier however may be capable of forming a stabilizing layer of lamellar liquid crystals around droplets of the primary oil-in-oil emulsion ($O_1/O_2$). This barrier film prevents coalescence between primary emulsion droplets and assists to preclude migration of the reactive component from the primary emulsion to the external aqueous phase.

The emulsifier included in the external aqueous phase has a low affinity for the oil phase. The emulsifier therefore does not disrupt the primary oil-in-oil emulsion ($O_1/O_2$) and avoids the formation of a simple oil-in-water emulsion.

Exemplary nonionic surfactants having an HLB value of greater than about 10 include, but are not limited to, trideceth-6, ceteth-10, laureth-9, octoxynol-9, nonoxynol-12, a poloxamer, trideceth-12, oleth-20 and polysorbate-20. Numerous other nonionic surfactants having an HLB value of greater than about 10 are listed in *McCutcheon's Emulsifiers and Detergents, North American and International Editions,* MC Publishing Co., Glen Rock N.J., pages 235–246 (1993).

Exemplary cationic surfactants include, but are not limited to, lauryl dimethyl amine oxide, stearyl dimethyl amine oxide, cocoamidopropyl dimethylamine oxide, stearamidopropyl dimethylamine, $C_{14-20}$ isoalkylamidopropylethyldimonium ethosulfate, $C_{18-22}$ isoalkylamidopropylethyldimonium ethosulfate, cocamidopropyldimonium hydroxypropylamino hydrolyzed animal protein, hydroxyanthraquinoneaminopropyl methyl morpholinium methosulfate, oleamidopropyl ethyldimonium ethosulfate, rapeseedamidopropyl benzyldimonium chloride, rapeseedamidopropyl ethyldimonium ethosulfate, ricinoleamidopropyl ethyldimonium ethosulfate, soyamidopropyl benzyldimonium chloride, soyamidopropyl ethyldimonium ethosulfate, stearamidopropalkonium chloride, stearamidopropyl cetearyl dimonium tosylate, and mixtures thereof.

Exemplary anionic surfactants include, but are not limited to, compounds having a hydrophobic moiety, such as a carbon chain including from about eight carbon atoms to about 30 carbon atoms, and particularly from about twelve carbon atoms to about twenty carbon atoms; and further includes a hydrophilic moiety, such as sulfate, sulfonate, carbonate, phosphate or carboxylate. Often, the hydrophobic carbon chain is etherified, such as with ethylene oxide or propylene oxide.

Suitable anionic surfactants include compounds in the classes known as alkyl sulfates, alkyl ether sulfates, alkylamide sulfates, alkylaminde ether sulfates, alkyl ether sulfonates, alkylamide sulfonates, sulfate esters of an alkyl carbonates, alkyl ether carboxylates, fatty acids, soaps, alkyl sulfosuccinates, alkyl ether sulfosuccinates, alkylamide sulfosuccinates, sarcosinates, alkyl phosphates, octoxynol or nonoxynol phosphates, taurates, fatty taurides, sulfated monoglycerides, fatty acid amido polyoxyethylene sulfates, isethionates, and mixtures thereof.

Usually, the anionic surfactant is present in the composition as a neutralized salt in the form of a sodium, potassium, lithium, ammonium, alkylammonium or hydroxyalkylammonium salt, wherein the alkyl moiety includes from one to about three carbon atoms. The alkyl sulfates and alkyl ether sulfates are particularly effective classes of anionic surfactants. Consequently, exemplary anionic surfactants include, but are not limited to, the ammonium, monoethanolmine, diethanolamine, triethanolamine, isopropylamine, sodium, potassium, lithium or magnesium salt of lauryl sulfate, dodecylbenzenesulfonate, lauryl sulfosuccinate, lauryl ether sulfate, lauryl ether carboxylate, lauryl sarcosinate, cocomethyl tauride, sulfosuccinate half ester amide, and mixtures thereof. Examples of especially useful anionic surfactants are a lauryl sulfate salt and a lauryl ether sulfate salt.

Exemplary amphoteric surfactants include, but are not limited to, cocoamidopropyl dimethyl betaine, cocoamidopropyl hydroxysultaine, cocodimethyl betaine, coco imidazoline dicarboxylate, coco imidazoline monocarboxylate, cocobetaine, lapyrium chloride, lauryl sultaine, decyl betaine, oleamidopropyl betaine, tallowamidopropyl betaine, sodium caproamphacetate, sodium lauroamphoacetate, sodium cocamphopropylsulfonate, numerous other alkylamido alkylamines and betaines listed in the *CTFA Cosmetic Ingredient Handbook,* 1$^{st}$ Ed., 1988 at pages 9, 10, 15 and 16.

Many additional nonionic, cationic, anionic, and amphoteric surfactants are listed in McCUTCHEON'S EMULSIFIERS AND DETERGENTS, 1993 ANNUAL, published by McCutcheon Division, MC Publication Co., Glen Rock, N.J., and in the *CTFA Handbook*.

In addition, a surfactant system capable of forming a liquid crystal structure also can be used as the emulsifier in the external aqueous phase (W). The surfactant system can be a single surfactant or a blend of surfactants. In some cases, a particular surfactant cannot form a liquid crystal structure alone, but can participate in the formation of liquid crystals in the presence of a second surfactant. Such a surfactant system forms a layer of lamellar liquid crystals around the primary oil-in-oil emulsion ($O_1/O_2$) to provide a barrier between the primary emulsion and the external aqueous phase. This type of an emulsion is different from the conventional emulsions which rely upon the orientation of the hydrophobic and hydrophilic components of a surfactant at an oil-water interface. The formation of a layer of lamellar liquid crystals around the primary oil-in-oil emulsion ($O_1/O_2$) can be detected by the presence of Maltese crosses viewed by optical microscopy through crossed polarizing plates or by freeze fracture electron microscopy.

As previously described, the HLB value of a surfactant is an approximate measurement of the solubility of a surfactant in water or oil. However, an HLB value is used only when the concentration of a surfactant in solution is sufficiently low such that a molecular monolayer of the surfactant is formed around droplets dispersed in a continuous phase, i.e., around the primary oil-in-oil emulsion ($O_1/O_2$). At higher surfactant concentrations, the surfactant can undergo a phase transition and the oil droplets then can be surrounded by a layer of lamellar liquid crystals, which can improve emulsion stability. The liquid crystals are localized at the oil/water interface and have been observed by microscopy techniques.

Exemplary classes of surfactants capable of participating in the formation of a liquid crystal structure around the primary oil droplets to stabilize the water-in-oil emulsion composition include, but are not limited to specific cationic surfactants, anionic surfactants, nonionic surfactants, quaternary ammonium surfactants and lipid surfactants.

Specific nonionic surfactants are fatty alcohols or fatty acids, or derivatives thereof, or a mixture of any of these, having a chain length of from about 14 to about 20 carbon atoms. These materials may be predominantly linear or may be branched. Some examples include myristyl alcohol, myristic acid, cetyl alcohol, palmitic acid, cestearyl alcohol, stearyl alcohol, stearic acid, oleic acid, oleyl alcohol, arachidyl alcohol, arachidic acid, and mixtures thereof.

Other specific non-ionic surfactants include condensation products of aliphatic ($C_{16}$ to $C_{22}$) primary or secondary linear or branched chain alcohols or phenols with alkylene oxides, usually ethylene oxide, and generally having from 1 to 30 ethylene oxide groups. Some examples include, but are not limited to, ceteth-1, ceteth-2, ceteth-3, ceteth-4, ceteth-5, ceteth-6, ceteth-10, ceteth-12, ceteth-14, ceteth-15, ceteth-16, ceteth-20, ceteth-24, ceteth-25, ceteth-30, ceteareth-2, ceteareth-3, ceteareth-4, ceteareth-5, ceteareth-6, ceteareth-7, ceteareth-8, ceteareth-9, ceteareth-10, ceteareth-11, ceteareth-12, ceteareth-13, ceteareth-14, ceteareth-15, ceteareth-16, ceteareth-17, ceteareth-18, ceteareth-20, ceteareth-22, ceteareth-23, ceteareth-24, ceteareth-25, ceteareth-27, ceteareth-28, ceteareth-29, ceteareth-30, steareth-2, steareth-3, steareth-4, steareth-5, steareth-6, steareth-7, steareth-8, steareth-10, steareth-11, steareth-13, steareth-14, steareth-15, steareth-16, steareth-20, steareth-21, steareth-25, steareth-27, steareth-30, arachideth-20, beheneth-5, beheneth-10, beheneth-20, beheneth-25, beheneth-30 and mixtures thereof.

Specific cationic surfactants include quaternary ammonium halides, e.g., alkyltrimethylammonium halides in which the alkyl group has from about 12 to 22 carbon atoms, for example dodecyltrimethyl-ammonium chloride, hexadecyltrimethylammonium chloride, cetyltrimethylammonium chloride, behenyltrimethylammonium chloride, benzyltrimethylammonium chloride, octyldimethylbenzyl-ammonium chloride, decetyldimethylbenzylammonium chloride, stearyldimethylbenzylammonium chloride, distearyldimethylammonium chloride, didodecyldimethylammonium chloride, dioctadecyldimethylammonium chloride, tallow trimethylammonium chloride, cocotrimethyl-ammonium chloride, cetylpyridinium chloride and their other corresponding halide salts and hydroxides. Preferred cationic surfactants are cetyltrimethylammonium chloride (CTAC) and cetyltrimethylammonium bromide (CTAB). CTAB 99% from Fluka, CTAC 50% (Arquad 16–50, Akzo). Preferably, cationic surfactants are used at 2–10% with CTAC and CTAB being the preferred cationic surfactants. Additionally, when mono-alkyl substituted cationic surfactants are used, it is preferred to also employ cholesterol wherein the ratio of cholesterol to cationic surfactant ranges from 0.1:1.0 to 1.0:1.0, more preferably from 0.5:1.0 to 1.5:1.0, and most preferably 0.7:1.0 to 1.25:1.0.

Specific anionic surfactants are di-alkyl sulfonates, di-alkyl ether sulfonates, di-alkylaryl sulfonates, di-alkanoyl isethionates, di-alkyl succinates, di-alkyl sulfosuccinates, di-N-alkoyl sarcosinates, di-alkyl phosphates, di-alkyl ether phosphates, di-alkyl ether carboxylates, and di-alpha-olefin sulfonates, especially their sodium, magnesium, ammonium and mono-, di- and triethanolamine salts. The alkyl and acyl groups generally contain from 12 to 20 carbon atoms and may be unsaturated.

The stabilizing liquid crystals may also be formed from lipid surfactants including either phospholipids, i.e., based on glycerol and sphingosine, or glycolipid, i.e. based on sphingosine. Phospholipids are preferred with phosphatidyl choline (lecithin) being the preferred phospholipid. Of the alcohol moieties which comprise the phosphoglycerides, serine, choline and ethanolamine are particularly preferred, and of the fatty chains, those having a chain length of $C_{14}$ to $C_{24}$ are preferred. The fatty acid chains may be branched or unbranched, saturated or unsaturated, and palmitic, myristic, oleic, stearic, arachidonic, linolenic, linoleic and arachidic acids are particularly preferred.

Preferred surfactants for the formation of liquid crystals in the aqueous continuous phase are of the nonionic type and include $C_{16-20}$ fatty alcohols, and $C_{16-20}$ fatty alcohol ethoxylates with 1 to 30 ethylene oxide groups. Specific examples include cetearyl alchol, cetyl alcohol, stearyl alcohol, arachidyl alcohol, oleyl alcohol, ceteareth ethoxylates with between 10 and 30 ethylene oxide groups, ceteth ethoxylates with between 10 to 30 ethylene oxide groups, steareth ethoxylates with between 10 and 30 ethoxylates, and combinations thereof. Preferably, $C_{16-20}$ fatty alcohols are used in combination with $C_{16-20}$ fatty alchol ethoxylates at a ratio of between 10:1 to 0.5:1, more preferably between 6:1 and 1:1, and most preferably between 5:1 and 1.5:1.

The external aqueous continuous phase (W) may comprise the emulsifier in an amount sufficient to stabilize the primary oil-in-oil emulsion ($O_1/O_2$). In one embodiment, the external aqueous continuous phase (W) comprises the emulsifier in an amount of from about 0% to about 15%, and more preferably from about 0.1% to about 10%, based on the weight of the external aqueous continuous phase.

Optional Components

The aqueous continuous phase of the emulsion treatment compositions according to the present invention may include optional benefit materials and cosmetic adjuncts, as long as the benefit materials or the adjuncts do not eliminate or substantially reduce the performance or chemical shelf stability of the reactive agent. The additional ingredients may include, for example dyes and coloring agents, fragrances; anionic, cationic, non-ionic, amphoteric or zwitterionic surfactants; buffers, masking fragrances, dispersing agents, stabilizers, cationic polymers, perfumes, non-ionic polymers, anionic polymers, complex coacervates, complex coacervate capsules, metal salts, lewis acids, buffering agents, particulate thickeners, polymeric thickeners, wax thickeners, oils, emollients, humectants, moisturizers, dyes, dyes and coloring agents, pearlescents, opacifiers, enzymes, suspending agents, antimicrobials, preservatives, proteins, herb and plant extracts, bleach, peroxide, polyols, silicones, oils, antibodies, pH adjusting agents including pH buffers, viscosity modifiers, preservatives, viscosity enhancers, gelling agents, chelators, silicones, emulsifying agents, moisturizing and conditioning agents, and other common adjuvants well known to those skilled in the art.

An antioxidant may also be incorporated within the emulsion treatment compositions. Suitable antioxidants include vitamin E and its derivatives, BHT and BHA.

In one embodiment of the present invention, a stabilizer comprising a polymeric thickener is employed. When polymeric thickeners are employed as the stabilizer in the emulsion treatment compositions herein, they are typically included in an amount ranging from about 0.01% to about 5%, preferably from about 0.3% to about 3%, based on the weight of the external aqueous phase (W). The polymeric thickener is preferably an anionic, nonionic, cationic or hydrophobically modified polymer selected from the group consisting of cationic polysaccharides of the cationic guar gum class with molecular weights of 1,000 to 3,000,000, anionic, cationic and nonionichomopolymers derived from acrylic and/or methacrylic acid, anionic, cationic and non-ionic cellulose resins, cationic copolymers of dimethyl-dialkylammonium chloride and acrylic acid, cationic homopolymers of dimethylalkyl-ammonium chloride, cationic polyalkylene and ethoxypolyalkylene imines, polyethylene glycol of molecular weight from 100,000 to 4,000,000, and mixtures thereof. Preferably, the polymer is selected from the group consisting of sodium polyacrylate, hydroxy ethyl cellulose, cetyl hydroxy ethyl cellulose, and Polyquaternium 10.

The polymeric thickener is preferably an anionic, nonionic, cationic or hydrophobically modified polymer of natural, modified natural or synthetic origin from plants, microbials, animals or petroleum raw materials including karaya gum, tragacanth gum, gum arabic, gum ghatti, guar gum, locust bean gum, quince seed, psyllium seed, tamarind seed, carrageenan, alginates, agar, larch gum, pectins, starches, xanthan gum, dextran, casein, gelatin, keratin, shellac, cellulose derivatives, guar derivatives, acrylic acid polymers, polyacrylamides, and alkylene/alkylene oxide polymers. Preferred polymeric thickeners include guar gum, available commercially as SUPERCOL U, U NF, SUPERCOL GF, SUPERCOL G2S, and SUPERCOL G3 NF from Aqualon and JAGUAR GUM from Rhone-Poulenc; xanthan gum, available commercially as KELTROL CG, KELTROL CG F, KELTROL CG T, KELTROL CG TF, KELTROL CG 1000, KELTROL CG RD, KELTROL CG GM, KELTROL CG SF, from Calgon, and RHODICARE S, RHODICARE XC, RHODICARE H, AND RHODICARE D, from Rhone-Poulenc; hydroxyethylcellulose, available commercially as NATRASOL 210 types and NATRASOL 250 types from Aqualon; hydroxypropyl guar, available commercially as JAGUAR HP-8, JAGUAR HP-11, JAGUAR HP-60, and JAGUAR H-79 from Rhone-Poulenc. Additional specific polymeric thickeners that are suitable for the present invention are given in *Rheological Properties of Cosmetics and Toiletries,* edited by Dennis Laba, 1993, Marcel Dekker, Inc., pages 57 through 121 (ISBN 0-8247-9090-1).

Alternatively, the stabilizer employed can comprise $C_{10}$–$C_{22}$ ethylene glycol fatty acid esters. $C_{10}$–$C_{22}$ ethylene glycol fatty acid esters can also desirably be employed in combination with the polymeric thickeners hereinbefore described. The ester is preferably a diester, more preferably a $C_{14}$–$C_{18}$ diester, most preferably ethylene glycol distearate. When $C_{10}$–$C_{22}$ ethylene glycol fatty acid esters are utilized as the stabilizer in the emulsion treatment compositions herein, they are typically present in an amount of from about 3% to about 10%, preferably from about 5% to about 8%, more preferably from about 6% to about 8%, based on the weight of the external aqueous phase (W).

For use, the composition may be provided at a pH from about 3 to 11, preferably from 4 to 10.

PRODUCT FORM

The emulsion treatment compositions according to the present invention may be provided in any suitable physical form, for example as low to moderate to high viscosity liquids, lotions, milks, mousses, dispersions, sprays, gels, foams, aerosols, and creams. These compositions may be produced by procedures well known to the skilled artisan. The emulsion compositions can be used in various manners as other known compositions in the art, including but not limited to, various rinse-off and leave-on applications such as hair shampoos, skin cleansers, skin lotions, hair conditioners, hair dyes, hair permanent waves, hair straighteners, hair bleaches, styling sprays, hair mousses, two-in-one shampoos, fabric softeners, lotions, nail polishes, hair serums, hair dyes, hair waving, etc.

The emulsion treatment compositions of the present invention can be formulated as a fluid, lotion, fluid cream or cream having a viscosity from 500 to 100,000 mPas or above. The compositions can be packaged in a suitable container to suit its viscosity and intended use by the consumer. For example, a lotion or fluid cream can be packaged in a bottle, a roll-ball applicator, a propellant-driven aerosol device, a container fitted with a pump suitable for hand or finger operation, or the like. When the composition is a cream, it can simply be stored in a non-deformable bottle or squeeze container, such as a tube or a lidded jar.

The emulsion treatment compositions of the present invention enable the formulation and delivery of reactive agents to amino acid based substrates from an aqueous composition that is chemically shelf stable.

METHOD OF USE

The emulsion treatment compositions of the present invention can be applied to wet hair, partially wet hair or dry hair. If desired, the compositions can be mixed with additional water or separate composition prior to or during application to the hair. The contact time between the emulsion treatment compositions of the present invention and the substrate can vary between 10 seconds and about 1 hour, preferably between 20 seconds and 30 minutes, more preferably between 30 seconds and 15 minutes. The compositions may be thoroughly rinsed from the hair, or the compositions can be applied as a leave-on product, as desired.

EXAMPLES

The following examples further describe and demonstrate various embodiments within the scope of the present invention. The examples are given solely for the purpose of illustration, and are not to be construed as limitations of the present invention since many variations thereof are possible without departing from its spirit and scope. In the examples and throughout the present specification, parts and percentages are by weight unless otherwise indicated. Ingredients are identified by chemical or CTFA name, or otherwise defined below.

The oil-in-oil-in-water ($O_1/O_2/W$) multiple emulsion treatment compositions of the present invention typically are prepared by a two step process. First, the reactive agent is solubilized within a suitable ($O_1$) oil/solvent and then the ($O_1$) oil/solvent comprising the reactive agent is emulsified within a suitable oil ($O_2$) to form the primary oil-in-oil emulsion ($O_1/O_2$). In preparing the primary oil-in-oil emulsion ($O_1/O_2$), the ($O_2$) phase particulate thickener with optional emulsifier (e1), is first added to the ($O_2$) oil with high shear and heat as described below. The ($O_1$) oil/solvent is then dispersed within the ($O_2$) oil phase under high shear conditions and preferably a high shear mixer (e.g., an IKA Ultra Turrax mixer, available from IKA Laboratories, Cincinnati, Ohio) until the ($O_1$) droplet particle size is between about 0.1 to about 10 microns in diameter.

Next, the resulting oil-in-oil emulsion is emulsified within the aqueous continuous phase (W) to form the multiple emulsion ($O_1/O_2/W$). The primary oil-in-oil emulsion is dispersed within the aqueous continuous phase using low shear mixing (e.g., less than 500 rpm on a bench scale mixer). Intensive, high shear mixing is avoided during this manufacturing step as it has a tendency to destroy the primary emulsion and release the contents of the internal ($O_1$) phase.

In the following Examples I–VI, the external aqueous continuous phase (W) is a fatty alcohol cream base having the following formula:

| External Aqueous Continuous Phase (W) | |
|---|---|
| Ingredient | Weight % of (W) |
| Ceteareth 25 (1) | 1.50 |
| Cetyl Alcohol (2) | 2.25 |
| Stearyl Alcohol (3) | 2.25 |
| Sodium Benzoate (4) | 0.09 |
| Phenoxyethanol (5) | 0.11 |
| Deionized water | 93.8 |

-continued

External Aqueous Continuous Phase (W)

| Ingredient | Weight % of (W) |
|---|---|

(1) available as Volpo CS25 from Croda Oleochemicals, North Humberside, England.
(2) available as CO-1695 from The Procter and Gamble Company, Cincinnati, Ohio.
(3) available as CO-1895 from The Procter and Gamble Company, Cincinnati, Ohio.
(4) available as Lactil from Goldschmidt, Hopewell, Virginia.
(5) available as Phenoxetol from Clariant Corp., Charlotte, North Carolina.

The external aqueous continuous phase is prepared according to the following procedure. In a suitable vessel, the deionized water is heated to about 80° C. while mixing. Next, the sodium benzoate, cetyl alcohol, stearyl alcohol and ceteareth 25 are added to the heated water. The resulting mixture is stirred at high speed (i.e., about 500 rpm on a lab scale mixer) while maintaining the temperature at approximately 80° C. After all of the ingredients are dispersed, mixing is continued for 30 minutes at approximately 80° C. Then the mixture is cooled to ambient temperature while mixing at a lower rpm.

Examples I–VI

The following Examples I–VI describe primary oil-in-oil emulsion compositions ($O_1/O_2$) used to prepare the multiple emulsion treatment compositions ($O_1/O_2/W$) of the present invention. All weight percentages in the following table are based on the total weight of the primary oil-in-oil emulsions ($O_1/O_2$).

TABLE I

Primary Emulsion Compositions ($O_1/O_2$)

| Ingredient | I | II | III | IV | V | VI |
|---|---|---|---|---|---|---|
| Reactive Agents | | | | | | |
| Polymer I (6) | 5.0 | 5.0 | 5.0 | 5.0 | — | — |
| Polymer II (7) | — | — | — | — | 5.0 | — |
| Conditioner III (8) | — | — | — | — | — | 5.0 |
| ($O_1$) Phase Oils/Solvents | | | | | | |
| D5 Cyclomethicone (9) | 45.0 | — | — | 45.0 | 45.0 | 45.0 |
| Propylene Carbonate (10) | — | 45.0 | 45.0 | — | — | — |
| ($O_2$) Phase Oils | | | | | | |
| Soybean Oil (11) | — | 45.0 | 45.0 | — | — | — |
| SEFA soyate/cottonate (12) | 45.0 | — | — | 45.0 | 45.0 | 45.0 |
| ($O_2$) Phase Thickeners | | | | | | |
| Tri-12-hydroxystearin (13) | 5.0 | 5.0 | — | — | 5.0 | 5.0 |
| Silica dimethyl silylate (14) | — | — | 5.0 | — | — | — |
| quaternium-18 hectorite (15) | — | — | — | 5.0 | — | — |
| | 100.0 | 100.0 | 100.0 | 100.0 | 100.0 | 100.0 |

(6) Polymer 1 is as described herein, the preparation of which can be referenced in U.S. Ser. No. 09/478,855 by R. Glenn et. al.
(7) Polymer 2 is as described herein, the preparation of which can be referenced in U.S. Ser. No. 5,525,332 by A. D. Gough et. al.
(8) Conditioner 3 is as described herein, the preparation of which can be referenced in U.S. Ser. No. 5,087,733 by T. M. Deppert et. al.
(9) available as Dow Corning 245 Fluid from Dow Corning Corporation, Midland, Michigan.
(10) available from Sigma Aldrich Chemical Company, item #P5,265-2.
(11) available from Sigma Aldrich Chemical Company, item #43,000-5.
(12) available from The Procter and Gamble Company, Cincinnati, Ohio.
(13) available as Thixcin R from Rheox, Inc., Hightstown, New Jersey.
(14) available as Aerosil R972 from Degussa Corporation, Ridgefield Park, NJ.
(15) available as Bentone 38 from Rheox, Inc., Hightstown, New Jersey.

Each of the exemplified oil-in-oil compositions is prepared according to the following procedure. The reactive agent is first added to the ($O_1$) oil/solvent and stirred until fully solubilized. The ($O_2$) oil phase particulate thickener is then added to the ($O_2$) oil and the resulting mixture is heated to approximately 60° C. while stirring under high shear using an IKA Ultra Turrax mixer until fully dispersed/homogenous. This mixture is then cooled to ambient temperature. Next, the reactive component (($O_1$) oil/solvent plus reactive agent) is added to the cooled ($O_2$) oil plus thickener mixture while stirring under high shear using an IKA Ultra Turrax mixer until the ($O_1$) droplet particle size is less than 10 microns in diameter, preferably 1–5 microns in diameter.

The resulting cooled ($O_1/O_2$) primary emulsion is then added to the cooled external aqueous fatty alcohol cream base while stirring under low shear until the droplet particle size of the ($O_1/O_2$) primary emulsion is between about 10 to about 500 microns in diameter, preferably 20 to 50 microns in diameter.

The specific embodiments and examples set forth above are provided for illustrative purposes only and are not intended to limit the scope of the following claims. Additional embodiments of the invention and advantages provided thereby will be apparent to one of ordinary skill in the art and are within the scope of the claims.

What is claimed is:

1. An emulsion treatment composition comprising:
    a) an aqueous continuous phase; and
    b) a discontinuous phase in the form of an oil-in-oil emulsion, the discontinuous phase comprising:
        i) a reactive component comprising a reactive agent and an internal oil, wherein the internal oil solubilizes the reactive agent, and
        ii) a middle oil in which the reactive component is dispersed, wherein the middle oil is immiscible with the internal oil, does not solubilize the reactive agent, is immiscible in the aqueous continuous phase, and includes from about 1% to about 30% by weight of a hydrophobic particulate thickener in said middle oil.

2. The emulsion treatment composition according to claim 1, wherein the reactive agent is covalently reactive with a keratin substrate.

3. The emulsion treatment composition according to claim 2, wherein the reactive agent is covalently reactive with human hair.

4. The emulsion treatment composition according to claim 3, wherein the reactive agent comprises one or more reactive groups selected from the group consisting of electrophilic groups, nucleophilic groups, protected thiol groups, and mixtures thereof.

5. The emulsion treatment composition according to claim 4, wherein the reactive agent further comprises a cosmetically active functional group.

6. The emulsion treatment composition according to claim 4, wherein said reactive agent comprises at least one electrophilic reactive group, said reactive agent being selected from the group consisting of halotriazine, haloquinoxaline, halopyrimidine, vinylsulfone, β-haloethylsulfone, β-sulfatoethylsulfone, acrylate, methacaylate, acrylamide, methacrylamide, maleimide, epoxide, acylhalide, ester, carbamate, dithiocarboxylic acid ester, alkoxysilane, thiosulfate, anhydride, urea derivative, isotbiocyanate, isocyanate, lactone, isothiuronium, and azlactone electrophilic groups, and mixtures thereof.

7. The emulsion treatment composition according to claim 4, wherein the nucleophilic reactive group is selected from the group consisting of thiols, thiolates, thiol-containing quaternary salts, thiolate-containing quaternary salts, thioalkyl esters, thiolalkylamides, thiol derivatives of cysteamine, thiolate derivatives of cysteamine, and mixtures thereof.

8. The emulsion treatment composition according to claim 4, wherein the protected thiol reactive group has the general formula:

R—(S—Pr)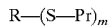

wherein R is a monovalent or multivalent cosmetically active functional group, S is sulfur, Pr is a protecting group and m is an integer from 1 to 100.

9. The emulsion treatment composition according to claim 8, wherein the protected thiol reactive group is selected from the group consisting of heterocyclic protecting groups, sp² aliphatic trigonal carbon protecting group, sp³ carbon electrophilic protecting groups, phosphorus protecting groups, metal based protecting groups, non-metal and metalloid based protecting groups other than phosphorus, energy-sensitive protecting groups, and mixtures thereof.

10. The emulsion treatment composition according to claim 1, wherein the composition comprising from about 0.01% to about 10% by weight of the emulsion treatment composition of the reactive agent.

11. The emulsion treatment composition according to claim 1, wherein the internal oil comprises a non-polar solvent selected from the group consisting of volatile silicone compounds, nonvolatile silicone compounds, volatile hydrocarbons, nonvolatile hydrocarbons, and mixtures thereof.

12. The emulsion treatment composition according to claim 1, wherein the internal oil comprises a polar solvent selected from the group consisting of amides, estees, ethers, ketones, cyclic amides, cyclic esters, cyclic ketones, cyclic ethers, and mixtures thereof.

13. The emulsion treatment composition according to claim 1, wherein the composition comprises from about 10% to about 80%, by weight of die oil-in-oil emulsion, of the internal oil.

14. The emulsion treatment composition according to claim 1, wherein the middle oil comprises an oil selected from the group consisting of fatty acid derivatives, di- and tri-glycerides, vegetable oil derivatives, liquid non-digestible oils and mixtures thereof.

15. The emulsion treatment composition according to claim 1, wherein the composition comprises from about 25% to about 80%, by weight of the oil-in-oil emulsion, of the middle oil.

16. The emulsion treatment composition according to claim 1, wherein the composition comprises from about 3% to about 20%, by weight of the middle oil phase, of the hydrophobic particulate thickener.

17. The emulsion treatment composition according to claim 16, wherein the thickener comprises a crystalline, hydroxyl-containing stabilizer selected from the group consisting of:

(i)
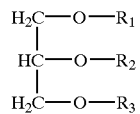

wherein
R₁ is

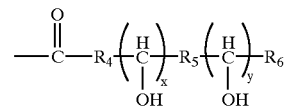

R₂ is R₁ or H,
R₃ is R₁ or H,
R₄ is a single bond or C$_{1-20}$ alkyl,
R₅ is a single bond or C$_{1-20}$ alkyl,
R₆ is H or C$_{1-20}$ alkyl, and
R₄+R₅+R₆=C$_{0-22}$,
and wherein 1≦x+y≦4;

(ii)
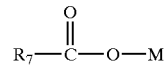

wherein R₇ is —R₄(CHOH)$_x$R₅(CHOH)$_y$R₆, wherein R₄, R₅, R₆, x and y are as defined above; and M is Na⁺, K⁺, Mg⁺⁺, or H; and (iii) mixtures thereof.

18. The emulsion treatment composition according to claim 16, wherein the hydrophobic particulate thickener comprises a hydrophobically modified dispersed amorphous silica or a hydrophobically modified dispersed smectite clay.

19. The emulsion treatment composition according to claim 1, wherein the aqueous continuous phase comprises water and stabilizing liquid crystals.

20. The emulsion treatment composition according to claim 1, wherein the composition comprises from about 45% to about 90%, by weight of the composition, of the aqueous continuous phase.

21. An emulsion treatment composition comprising:
a) from about 50% to about 85%, by weight of the emulsion treatment composition, of an aqueous continuous phase; and
b) from about 10% to about 50%, by weight of the emulsion treatment composition, of a discontinuous phase in the form of an oil-in-oil emulsion, the discontinuous phase including
  i) a reactive component including from about 1% to about 5%, by weight of the emulsion treatment composition, of a reactive agent and from about 25% to about 60%, by weight of the oil-in-oil emulsion, of an internal oil, wherein the internal oil solubilizes the reactive agent, and
  ii) from about 40% to about 60%, by weight of the oil-in-oil emulsion, of a middle oil in which the reactive component is dispersed, wherein the middle oil is immiscible with the internal oil, does not solubilize the reactive agent, is immiscible in the aqueous continuous phase, and comprises from about 5% to about 15%, by weight of the middle oil, of a hydrophobic particulate thickener.

22. A method for treating hair, which method comprises applying an effective amount of the emulsion treatment composition of claim 3 to the hair.

* * * * *